(12) United States Patent
Levisman

(10) Patent No.: US 7,490,723 B2
(45) Date of Patent: Feb. 17, 2009

(54) EASY-TO-OPEN GLASS AMPOULE AND DEVICE

(76) Inventor: Ricardo Levisman, 1292 Agüero St. 1st Floor, 1425 Buenos Aires (AR)

( * ) Notice: Subject to any disclaimer, the term of this patent is extended or adjusted under 35 U.S.C. 154(b) by 814 days.

(21) Appl. No.: 10/876,323

(22) Filed: Jun. 23, 2004

(65) Prior Publication Data

US 2005/0287045 A1    Dec. 29, 2005

(51) Int. Cl.
*A61J 1/06* (2006.01)
*B67B 7/92* (2006.01)

(52) U.S. Cl. .......... 206/368; 206/63.5; 215/47; 215/49; 422/102; 225/93; 241/99

(58) Field of Classification Search .......... 422/102; 222/92, 107, 541.1–541.9; 65/61, 102; 215/47, 215/49, 901, 48; 225/93, 96.5, 97, 103
See application file for complete search history.

(56) References Cited

U.S. PATENT DOCUMENTS

| | | | | |
|---|---|---|---|---|
| 2,517,604 A | * | 8/1950 | Smith | 215/49 |
| 2,638,022 A | * | 5/1953 | Reyes | 225/93 |
| 2,659,253 A | * | 11/1953 | Myrick | 225/93 |
| 3,640,437 A | * | 2/1972 | Galy | 225/96.5 |
| 3,739,966 A | * | 6/1973 | Lynn | 226/30 |
| 3,749,271 A | * | 7/1973 | Ellis et al. | 215/47 |
| 4,506,817 A | * | 3/1985 | Parker | 225/96.5 |
| 4,979,630 A | * | 12/1990 | Rose et al. | 215/47 |
| 5,379,898 A | * | 1/1995 | Joulia | 206/528 |

FOREIGN PATENT DOCUMENTS

GB    1188555 A    *    8/1967

* cited by examiner

*Primary Examiner*—Jill Warden
*Assistant Examiner*—Cedric A Chan
(74) *Attorney, Agent, or Firm*—Greer, Burns & Crain, Ltd.

(57) ABSTRACT

A glass ampoule for packaging and containing solid matter under sterile conditions, the glass ampoule comprising an integral glass body having a breaking section, the breaking section being breakable to define an opening large enough to easily remove the matter.

9 Claims, 4 Drawing Sheets

EASY-TO-OPEN GLASS AMPOULE AND DEVICE

BACKGROUND OF THE INVENTION

1. Field of the Invention

The present invention relates to a new packaging for sterilized matter and more particularly relates to a new glass ampoule for containing medical matter and preferably medical devices, wherein the medical device is preferably kept packaged under aseptic and sterilized conditions and the ampoule is easily and safely opened to permit an easy and quick removal of the medical device out from the ampoule.

2. Description of the Prior Art

Glass ampoules are very well known in the medical field for containing liquids such as pharmaceuticals, solutions and the like, for injections for example, wherein the ampoule comprises a glass body having a main cylindrical portion having a large diameter and a smaller portion with a smaller diameter, both portions being connected through a neck portion with a very small diameter provided to define a breaking section. All these portions are hollow and the user must file or cut down all around the neck portion to then break the ampoule at the neck section by exerting a force with the fingers.

Generally, the glass ampoules need a very small neck portion to concentrate the stresses of breaking forces applied by the user, whereby the ampoule breaks at the neck section, namely the section with the largest stress concentration. As explained, the diameter at the neck section must be very small, therefore when the ampoule is broken a very small opening is defined. While this is not a drawback when the matter contained in the ampoule is a liquid, because the liquid may be easily poured through the small opening, the diameter of such opening is insufficient when a solid product packaged in the ampoule must be removed out of the ampoule.

Considering that the glass is capable of keeping inner sterile condition into the container for many years, the use of a glass container has been extended not only for liquid matter but also for solid matter. Dental implants and other medical devices have been packaged into glass containers, some of them pretending to be a kind of glass ampoules but these containers are not completely made of glass. While the most part of these containers are made of glass, an opening large enough to permit the removal of the contained solid product is provided and the opening is closed and sealed by a cap or plug. However, all the materials used for the plug or cap have failed to provide an effective seal to keep the inner sterile conditions for a long period of time.

Therefore, it would be very convenient to have a container integrally made of glass, such as a glass ampoule, for keeping under effective sealed sterile conditions any desired matter for long periods of time, with the container being provided with means for defining an opening permitting the easy removal of the packaged matter, particularly when the matter is a solid device, such as a medical graft, dental implant, and the like.

SUMMARY OF THE INVENTION

It is therefore an object of the present invention to provide a sealed container for packaging and containing a matter under sterile conditions and for remarkable extended periods of time.

It is still another object of the present invention to provide a glass ampoule for packaging and containing solid matter under sterile conditions, the glass ampoule comprising an integral glass body having a breaking section, the breaking section being breakable to define an opening large enough to easily remove the matter.

It is a further object of the present invention to provide an easy-to-open glass ampoule for containing matter under controlled packaging conditions, the glass ampoule comprising a hollow portion for housing the matter and a solid glass breaking portion for breaking the portions apart to open the ampoule.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

The invention may be better understood with reference to the following description which is not limitative or restrictive of the scope of protection. On the contrary, it must be clearly understood that many other embodiments, modifications and alterations equivalent to the elements of the invention may be suggested by persons skilled in the art after reading the present description, without departing from the spirit of the present invention and/or the scope of the appended claims.

DESCRIPTION OF THE PREFERRED EMBODIMENTS

Now referring in detail to the invention, the same refers to a new container, namely a glass ampoule 1, capable of packaging and containing a matter, preferably a medical matter and more preferably a medical device 2, such as an implant, under desired controlled conditions, such as sterile conditions, and capable of permitting an easy and safe opening of the ampoule to have a clear access to the medical device packaged into the ampoule. While reference to a dental implant 2 will be made, the ampoule may contain any other medical device, as well as either a solid, a liquid or a combination thereof. In addition, the matter may be packaged under vacuum conditions or in a controlled atmosphere, such as with a desired gas. The medical device may be sterilized by gamma radiation once already packaged in the ampoule.

Figure 4:
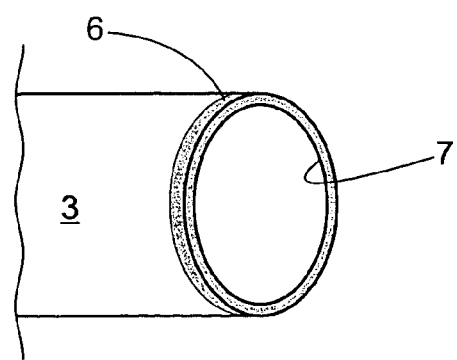
FIG. 4 shows a partial cross-sectional perspective view of the opening defined in the hollow portion of the ampoule.

The inventive ampoule is made of glass, preferably translucent or transparent glass, such as borosilicate glass, and comprises a hollow portion 3 for accommodating and containing medical device 2, and a solid breaking portion 4. The combination of hollow portion 2 and breaking portion 4 permits, at a connection thereof, a neat breaking of portions apart to open the ampoule. More particularly, hollow portion 3 is a cylindrical portion with the largest length thereof preferably having a constant diameter or cross-section to accommodate device 2. Portion 3 is comprised of thin glass walls that suddenly merge, through a merging section or portion 5, into a thick solid body of glass that defines breaking portion 4. While a neat breaking of the ampoule would be obtained at the merging section 5, namely the connection between portions 3 and 4, a breaking line 6 is defined in the thin wall of hollow portion 3, at merging portion 5, close to the solid glass body of breaking portion 4. Line 6 is made by filing for example, in order to have a weakened section in the glass wall thickness, whereby the line defines an easy and neat cut in the hollow portion to break the portions apart in order to define a wide and clear opening 7, FIG. 4. Distinct from the prior art ampoules, opening 7 is formed in the largest diameter or section of the hollow portion of the ampoule thus defining a clear and wide opening having a dimension enough for easily removing medical device 2 therethrough.

When the medical device comprises a dental implant or osteosynthesis screw, the implant is preferably provided with an implant body 2a and a wrench 2b connected at a top portion of body 2a. Wrench 2b is for inserting the implant into a bone hole in the patient and to screw the implant into the hole. To easy this work, a grip portion 2c is connected to wrench 2b with portion 2c having a diameter or dimension enough to be retained into ampoule 2 as illustrated but free enough to be easily removed from the ampoule.

Figure 1:
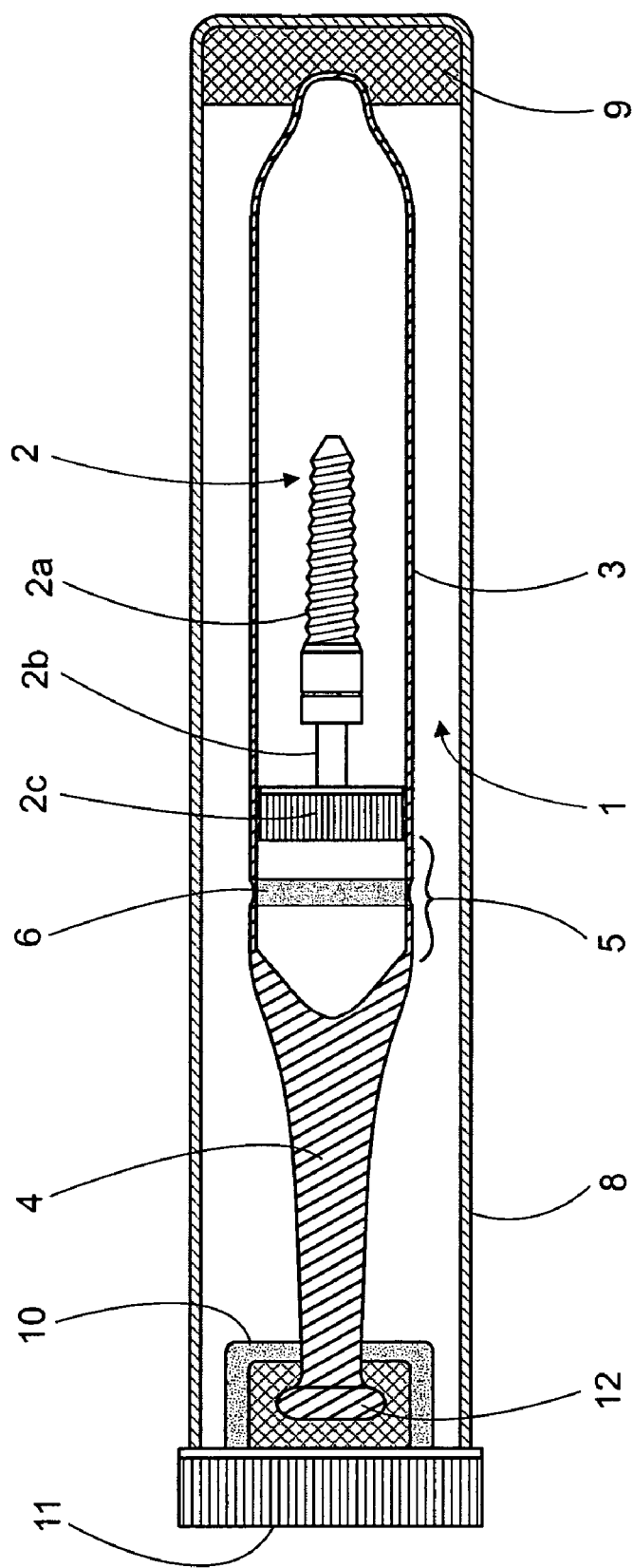
FIG. 1 shows a cross sectional view of a packaging including a glass ampoule according to a preferred embodiment of the invention.
Figure 2:
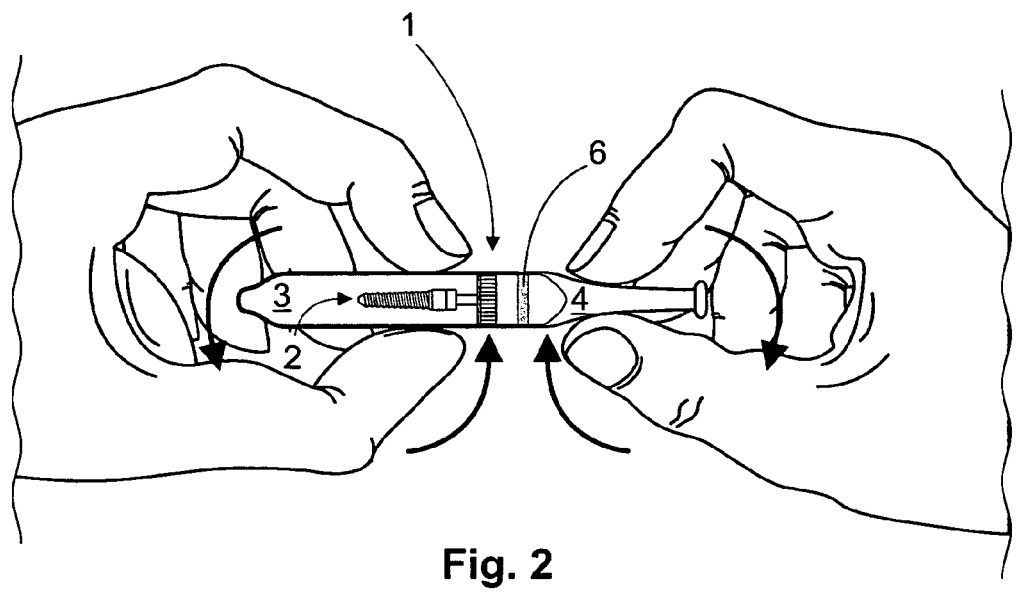
FIG. 2 shows a side elevational view of the inventive ampoule of FIG. 1 during a breaking action in the hands of a user.
Figure 3:
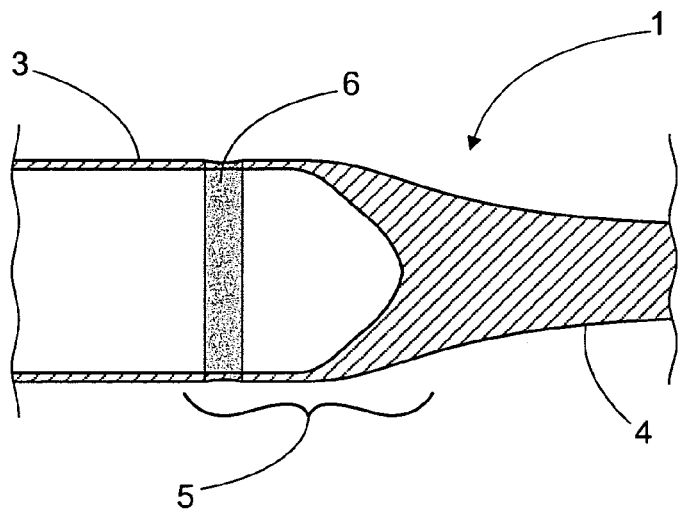
FIG. 3 shows a partial cross-sectional view of the breaking section, or breaking portion, of the inventive ampoule.

Preferably, ampoule 1 is made of one piece of glass and it may be manufactured from a glass tube that is heated to close one end thereof and to form solid portion 4 at another opposite end. Solid portion 4 also forms a kind of handle to be gripped by the fingers of a user, whereby the ampoule is broken at the breaking section by exerting forces as indicated in FIG. 2.

In order to commercialize, transport and handle the inventive ampoule under safe conditions, the ampoule may be packaged into an outer container 8 that may be made of any appropriate material such as plastics. The container may include one 9 or more resilient inserts for retaining ampoule 1 duly spaced apart from the container walls and kept under protection against any falling down of container 8 and any shock thereon. Container 8 may be sealed by a cap 11. While container 8, made of plastics, may fail in maintaining the interior thereof sterile for long periods of time, the medical device is always kept under sterile conditions by the glass ampoule. Additionally, ampoule 1 may be provided with a button 12 that facilitates the retention of portion 4 either into the container by means 10 as well as by the fingers of the user when manipulated.

As illustrated in FIGS. 5-8, the invention also provides practical devices for opening the ampoule. According to a preferred embodiment, illustrated in FIGS. 5, 6, the inventive breaking device comprises two cylindrical portions 13, 14, connected to each other by hinge means 15 for moving the cylindrical portions between an aligned position, FIG. 5, for receiving a sealed ampoule, and a relative angular position, FIG. 6, wherein the ampoule is broken apart into two parts, namely hollow portion 3 and breaking solid portion 4.

Figure 5:
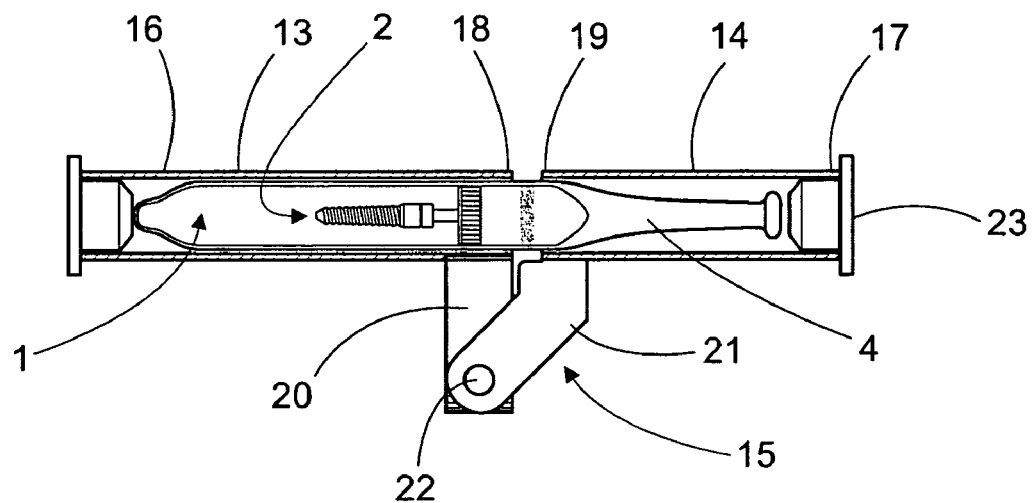
FIG. 5 shows a cross-sectional side elevational view of a breaking device for opening glass ampoules, according to a preferred embodiment of the invention, in a first operative position.
Figure 6:
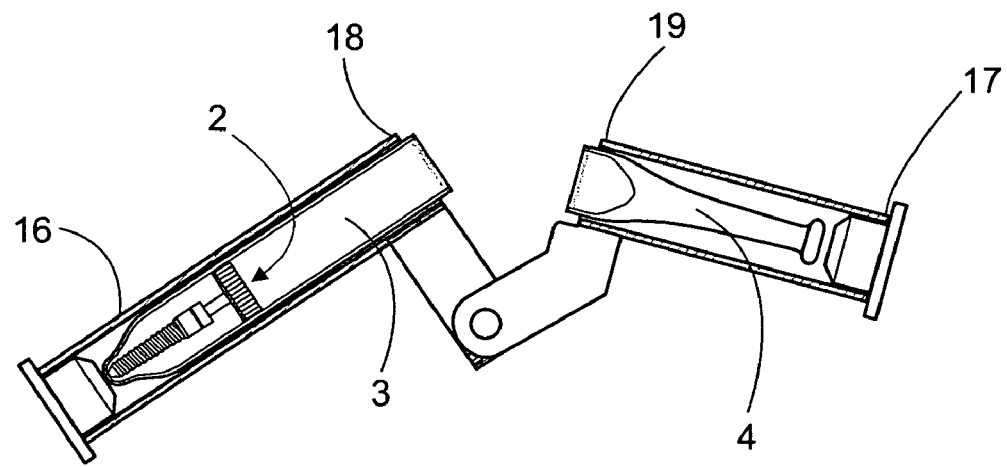
FIG. 6 shows a cross-sectional side elevational view of the breaking device of FIG. 5 in a second operative position.

Each cylindrical portion 13, 14, has a proximal end 16, 17, and a distal end, 18, 19, with the hinge means being connected to the portions close to the proximal ends. Hinge means comprises arms 20, 21 each one connected, by welding for example, to the associated cylindrical portion 13, 14, and pivotally connected to each other through pivoting axis 22. Preferably, one end, such as distal end 17, may be closed by a plug 23 whereby the broken apart portion 4 of the ampoule remains retained within cylindrical portion 14. End 16 also may be closed by a similar plug but it is preferably open to permit the insertion of ampoule 1 into portions 13, 14 when the same are aligned as illustrated in FIG. 5.

Figure 7:
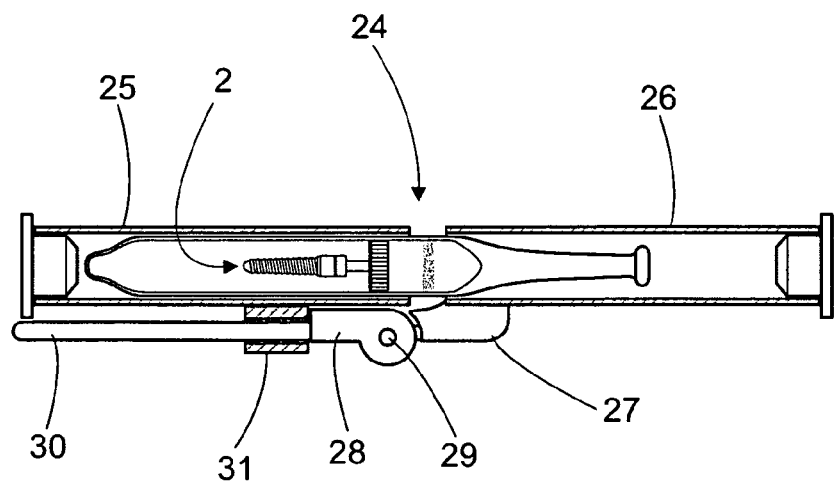
FIG. 7 shows a cross-sectional side elevational view of a breaking device for opening glass ampoules, according to another embodiment of the invention, in a first operative position.
Figure 8:
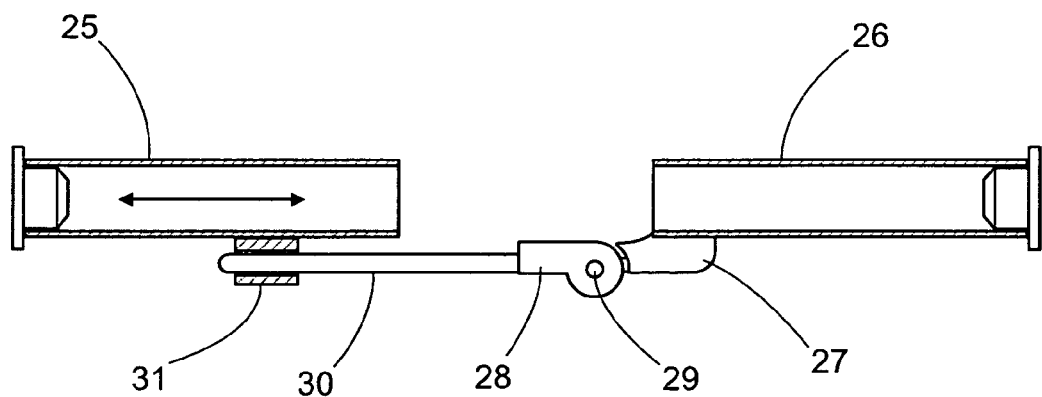
FIG. 8 shows a cross-sectional side elevational view of the breaking device of FIG. 7 in a second operative position.

In order to make the insertion of ampoule 1 easier, another device 24, shown in FIGS. 7, 8, comprises two cylindrical portions 25, 26 capable of moving away one from each other. Hinge means comprises one fixed arm connected, by welding for example, to one of the portions, such as portion 26, and a sliding arm 28, connected to the other portion 25. Both arms are pivotally connected through a pivoting axis 29. Arm 28 includes a sliding portion comprising one or more stems 30 slidably connected to a stationary block 31 fixed to the other cylindrical portion 25. Thus, the hinge means is extendable for moving apart the cylindrical portions relative to each other in order to facilitate introduction and/or extraction of an ampoule into and/or from the device. FIG. 8 shows device 24 in the extended position for inserting or removing an ampoule.

Breaking devices shown in FIGS. 5-8 may be manufactured of any convenient material such as rigid plastics, resins and stainless steel, etc.

While preferred embodiments of the present invention have been illustrated and described, it will be obvious to those skilled in the art that various changes and modifications may be made therein without departing from the scope of the invention as defined in the appended claims.

I claim:

1. An easy-to-open glass ampoule for containing matter under controlled packaging conditions, the glass ampoule comprising:
   a cylindrical portion with a largest length thereof having a constant cross-section and diameter, said cylindrical portion including an integral wall having an outer surface and a uniform thickness that defines a longitudinal, central hollow portion having a constant diameter;
   a breaking line defined on said outer surface of said cylindrical portion and having a thickness that is less than said thickness of said wall of said cylindrical portion;
   a solid glass portion including an integral wall and an outer surface continuing from said wall and said outer surface of said cylindrical portion, said solid glass portion forming a handle for gripping by fingers of a user to break the ampoule at said breaking line; and
   a sealed end portion opposite to said solid glass portion, wherein breaking the ampoule at said breaking line defines a clear, wide opening having a diameter that is substantially the same as said diameter of said hollow portion.

2. The ampoule of claim 1, wherein said breaking line is defined in said cylindrical portion close to said solid glass portion.

3. The ampoule of claim 1, wherein said breaking line is defined in a merging section between said solid glass portion and the length having the constant cross-section of said cylindrical portion.

4. A device for opening the ampoule of claim 1, the device comprising two cylindrical portions connected to each other by hinge means for moving between an aligned position for receiving the ampoule to be opened and a relative angular position for breaking the ampoule apart into two parts.

5. The device of claim 4, wherein each cylindrical portion has a proximal end and a distal end, with the hinge means being connected to the portions close to the proximal ends.

6. The device of claim 5, wherein the distal end of at least one of the portions is closed while the distal end of the other one of the portions is open to receive the ampoule.

7. The device of claim 4, wherein each cylindrical portion is made of stainless steel.

8. An easy-to-open glass ampoule for containing matter under controlled packaging conditions, the glass ampoule comprising a hollow portion for housing the matter and a solid glass portion, the hollow portion comprising thin glass walls that suddenly merge into a thick solid body of the solid glass portion for breaking the hollow and solid glass portions apart to open the ampoule, a breaking line being defined at a section of the hollow portion having the largest diameter to define, when broken, a clear and wide opening; and two cylindrical portions connected to each other by hinge means for moving between an aligned position for receiving the ampoule to be opened and a relative angular position for breaking the ampoule apart into two parts, the hinge means being extendable to move the cylindrical portions apart relative to each other in order to facilitate introduction and extraction of an ampoule into and from the device.

9. The device of claim 8, wherein the hinge means comprises a pivoting part connected to one of the cylindrical portions, the pivoting part including a sliding portion slidably connected to a stationary block connected to the other cylindrical portion.

* * * * *